United States Patent [19]

Mund et al.

[11] Patent Number: 4,505,784
[45] Date of Patent: Mar. 19, 1985

[54] METHOD FOR UREA ANALYSIS

[75] Inventors: Konrad Mund, Uttenreuth; Günter Luft, Lauf; Ulrich Gebhardt, Langensendelbach, all of Fed. Rep. of Germany

[73] Assignee: Siemens Aktiengesellschaft, Munich, Fed. Rep. of Germany

[21] Appl. No.: 399,246

[22] Filed: Jul. 19, 1982

[30] Foreign Application Priority Data

Jul. 29, 1981 [DE] Fed. Rep. of Germany ....... 3129988

[51] Int. Cl.³ ............................................. G01N 27/46
[52] U.S. Cl. .................... 204/1 T; 204/402; 204/403; 204/415
[58] Field of Search ............... 204/1 T, 1 K, 1 P, 432, 204/403, 415, 402

[56] References Cited

U.S. PATENT DOCUMENTS

| 2,805,191 | 9/1957 | Hersch | 204/402 |
| 3,067,384 | 12/1962 | Sorg | 204/413 |
| 3,523,883 | 8/1970 | Waclawik et al. | 204/402 |
| 3,707,455 | 12/1972 | Derr et al. | 204/415 |
| 3,770,607 | 11/1973 | Williams | 204/415 |
| 3,776,819 | 12/1973 | Williams | 204/403 |
| 3,926,734 | 12/1975 | Gray et al. | 435/12 |
| 4,090,926 | 5/1978 | Matson | 204/413 |

FOREIGN PATENT DOCUMENTS 1531761 11/1978 United Kingdom ............... 204/402

Primary Examiner—T. Tung
Attorney, Agent, or Firm—Kenyon & Kenyon

[57] ABSTRACT

For determining the urea concentration in liquids in continuous operation, with high sensitivity and reliable determination of the urea content over an extended period of time, an electrode which is separated from the urea containing liquid by means of a diaphragm with a diffusion coefficient of less than $10^{-7}$ cm$^2$ s$^{-1}$ for urea has impressed on it potentiostatically and cyclically, two potential values, the more positive potential being between 0.9 and 2.0. V/H$_2$rev and the more negative potential being lower than 0.6 V/H$_2$rev, and at the more positive potential, the current flowing within a predetermined time interval is evaluated as the measuring signal.

9 Claims, 2 Drawing Figures

METHOD FOR UREA ANALYSIS

BACKGROUND OF THE INVENTION

This invention relates to a method for determining the urea concentration in liquids as well as a urea sensor for carrying out the method.

The determination of the urea concentration is important, for instance, to kidney disease patients. For decontaminating the blood of these persons, i.e., for removing the urea from the blood, three methods are presently in use: hemodialysis, hemofiltration and peritonic dialysis. It is attempted here to free the urea containing electrolytes or blood filtrates which accumulate in these treatment methods, i.e., in the blood purification, of urea, so that the dialysis and substitution solutions which have been necessary heretofore, can be dispensed with. Then, however, it is of interest to see the result of the treatment and to indicate its end point, which necessitates an exact urea analysis.

Besides the methods mentioned above which have already been introduced, new methods for the elimination of urea are also being worked out such as electro adsorption or the so-called indirect urea oxidation. In this method also, it is necessary, however, to monitor the urea concentration, which requires reliable urea sensors.

It would also be of advantage if implantable urea sensors were available, because then the urea concentration in the blood of kidney disease patients could be monitored. A signal could then be released if a limit was reached and blood purification would be carried out.

Also for patients who suffer from diabetes, an exact urea determination would turn out to be advantageous. For, these persons could be helped with an implantable insulin dosing device, where a glucose sensor would make a control loop possible. However, the calibration curves of glucose sensors have so far been impaired by urea and therefore, an improvement could be achieved by a urea determination, i.e., the interference effect could be corrected.

Up to now, the urea content in (body) fluids has usually been determined intermittently by chemical analysis. Such a procedure, however, is unsatisfactory. While the urea concentration can also be determined continuously by means of an enzymatic sensor, the application is limited by the useful life of the enzyme membrane, and implantation is not possible.

It is an object of the present invention to provide a method for determining the urea concentration in liquids, which operates continuously, is sensitive, and permits a reliable determination of the urea content over long periods of time also.

SUMMARY OF THE INVENTION

According to the present invention, this is achieved by using an electrode which is separated from the urea containing liquid by a urea permeable diaphragm and impressing, by means of a reference and counter electrode cyclically and potentiostatically, two potential values thereon, the more positive potential being in the interval $0.9\ V \leq \phi/H_2\text{rev} \leq 2.0\ V$ and the more negative potential being lower than $0.6\ V/H_2\text{rev}$, and that for the more positive potential, the current flowing within a predetermined time interval is evaluated as the measuring signal.

The method according to the present invention uses an electrode arrangement wherein the urea is oxidized at the measuring electrode for the urea determination. An electrochemical method is therefore involved here. The diaphragm used in this method limits the diffusion. The diaphragm should have pores so fine that only small molecules such as urea, glucose and amino acids can penetrate into the diaphragm pores and migrate toward the electrode, while large molecules such as proteins are prevented from getting to the electrode surface.

In the method according to the present invention, the current flowing within a predetermined time interval, i.e., during the measuring period, is evaluated as the measuring signal. Preferably, the transferred charge is determined as the measuring signal, i.e., the current flowing during the measuring period is integrated. A certain urea concentration can then be assigned to the determined charge, since the measuring signal is proportional to the urea concentration.

It is essential in the method according to the present invention that the anodic current be measured at the more positive potential, at which the oxidation of the urea takes place. This potential is preferably around 1.6 V as measured against the reversible hydrogen electrode ($H_2$rev). Subsequently, a more negative potential is then impressed on the measuring electrode, which is preferably around $0.4\ V/H_2\text{rev}$. Here, the electrode surface and thereby, the reaction centers, are freed of blocking substances which are reduced. The potential of the measuring electrode is advantageously controlled by a cyclic potential-jump program with two levels, the measuring and the regeneration potential. The duration of the load depends on the diffusion coefficient and the thickness of the diaphragm; it is 5 to 10 minutes, at most.

Apparatus for implementing the method according to the present invention, a so-called electrochemical urea sensor, comprises a measuring electrode, a counter electrode and a reference electrode as well as a diaphragm which has a diffusion coefficient for urea at the operating temperature, e.g. body temperature, which is $\leq 10^{-7}\ cm^2\ s^{-1}$; the diaphragm is arranged in front of the measuring electrode. With such a sensor, selective urea determination is possible.

Preferably, the diaphragm has a diffusion coefficient for urea of about $10^{-11}\ cm^2\ s^{-1}$. For, it has been found that with decreasing permeability of the diaphragm, i.e., decreasing pore size, the ratio of the permeabilities to urea and glucose, which is 2 in the free electrolyte, changes. With a diffusion coefficient D for glucose of about $10^{-8}\ cm^2\ s^{-1}$, the D ratio (of urea to glucose) already has reached the value 10. With $D=10^{-10}\ cm^2\ s^{-1}$ for glucose, the D ratio is about 100. With such values, no interference of the urea determination with glucose takes place with certainty.

In the urea sensor according to the present invention, the thickness of the diaphragm is preferably less than or equal to 10 μm. In this manner a short response time of the sensor is achieved. It is of further advantage if the resistance of the diaphragm is no higher than 1 kohm $cm^2$ because then, the charge of the double-layer capacity of the measuring electrode can be reversed quickly.

Advantageously, the diaphragm is hydrophobic as well as hydrophilic, i.e., it has in part a hydrophobic and in part a hydrophilic character and thus is quasi-bivalent. Generally, the diaphragm consists of a hydrophobic polymer which is partly hydrophilic. In such diaphragms, the diffusion coefficients are influenced by the number of hydrophilic groups in the hydrophobic polymer chains. Substituents such as —OH, —COOH, —SO$_3$H and —NH$_3^+$ can be considered present as hydrophilic groups.

The diaphragms used in the urea sensor according to the present invention advantageously have a degree of hydrophilization H of between 1:15 and 1:100; and preferably between 1:30 and 1:60. "Degree of hydrophilization" as used herein means the ratio of hydrophilic groups to carbon atoms present. With degrees of hydrophilization in the range mentioned, the diffusion of urea is favored over that of glucose and amino acids.

The diaphragms consist advantageously of weakly hydrophilized polysulfone, preferably of weakly sulfonized polysulfone. Such polymers can be prepared by sulfonizing polysulfone with chlorosulfonic acid.

In the urea sensor according to the present invention, the measuring electrode advantageously consists of a noble metal, preferably platinum. As a reference electrode, a silver/silver chloride electrode is generally used. The counter electrode is advantageously an electrode with a large double-layer capacity, and in particular, an activated vitreous carbon electrode (see in this connection German Offenlegungsschrift No. 26 13 072, claims 1 to 4). Such electrodes are only slightly polarized, inhibit gas development and undesirable electrochemical reactions and keep the power requirements for the sensor low. In addition, the functions of the counter and the reference electrodes can be combined, i.e., the counter electrode serves at the same time as the reference electrode.

DETAILED DESCRIPTION

Figure 1:
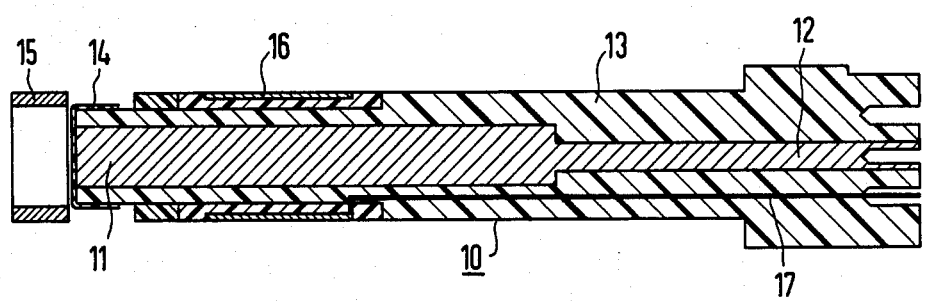
FIG. 1 is a cross section of a sensor according to the present invention.

In FIG. 1, an advantageous embodiment of the urea sensor according to the present invention is shown in a cross section. The rod shaped urea sensor 10 has a centrally arranged measuring electrode 11 in the form of a platinum pin. The measuring electrode 11, which has an extension 12 serving as a contact, is enclosed by an insulating plastic jacket 13, for instance, of polymethacrylate, where, however, the end of the platinum pin facing away from the extension 12 is exposed. At this end, the urea sensor is provided with a diaphragm 14 which covers the exposed surface of the measuring electrode 11. A ring shaped clamping cap 15 is used for the secure fixation of the diaphragm 14, as shown in FIG. 1. Besides the measuring electrode 11, an annular counter electrode 16 is embedded in the plastic jacket 13 in such a manner that its outer surface is exposed, i.e., is in contact with the environment. The counter electrode consists of vitreous carbon and acts at the same time as the reference electrode. A wire 17 is used to contacting the counter electrode 16.

A sensor of the above-mentioned type was used for determinating urea concentration. To adapt the tests carried out to the physiological conditions, especially the blood flow, as far as possible, the sensor was installed in continuous flow apparatus, the measuring electrode being exposed to the flow, and the counter electrode was therefore arranged behind the measuring electrode, flow wise. Tyrode solution served as the electrolyte liquid, a solution isotonic with blood (containing NaCl, KCl, CaCl$_2$, MgCl$_2$, NaH$_2$PO$_4$, NaHCO$_3$ and glucose in distilled water); this solution was flushed with a gas mixture consisting of 95% compressed air and 5% carbon dioxide.

For the measurements themselves, the measuring electrode is loaded for a given time, for instance, 50 seconds, at a potential of 1600 mV/H$_2$rev. Subsequently, a jump to a potential of 400 mV/H$_2$rev is made, which is likewise applied to the electrode for 50 seconds. In the process, the substances formed at the electrode are reduced. The urea which is not oxidized at this potential, diffuses to the exposed electrode surface and is adsorbed there. In the jump to the potential of 1600 mV/H$_2$rev (loading time: 50 seconds), the urea is then oxidized electrochemically, after the charge of the electrode capacities is reversed. The current then flowing is integrated and the integral obtained serves as the measuring value. The measuring value is obtained, for instance, by integration of the last 20 seconds.

Figure 2:
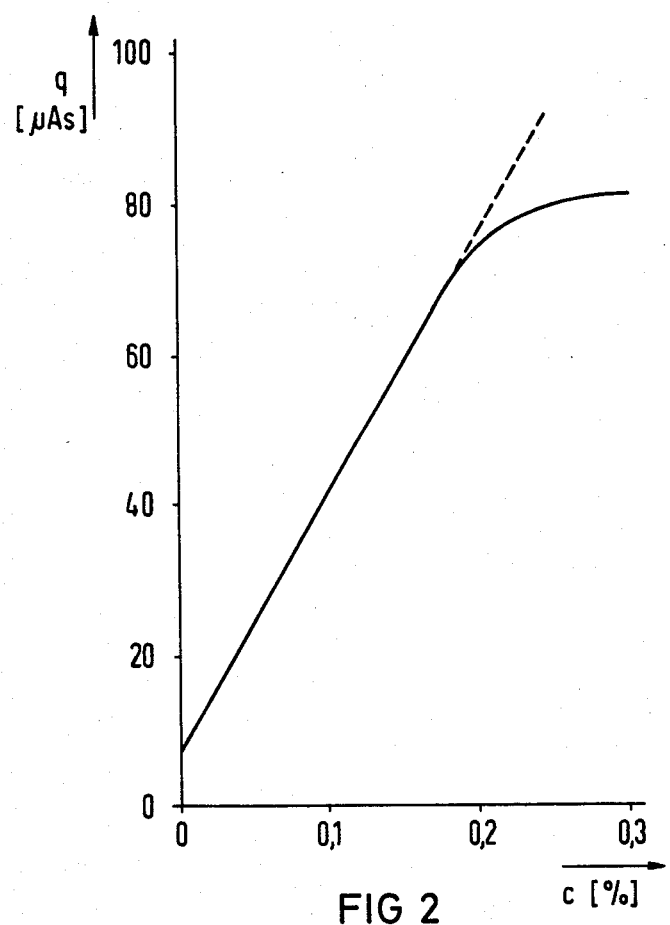
FIG. 2 is a curve illustrating the relationship between measured charge and urea concentration.

In FIG. 2, a calibration curve resulting from tests of the kind mentioned above, using different urea concentrations, is shown: the charge q (in $\mu$As) is plotted along the ordinate and the urea concentration c along the abscissa (in %). It will be seen from FIG. 2 that the charge determined is proportional to the urea concentration up to a value of about 0.2%, i.e., 200 mg/dl. This value is approximately 10 times the average physiological concentration of urea in the human body.

In the tests described above, a platinized platinum electrode with an exposed surface of 0.125 cm$^2$ was used as the measuring electrode. A sulfonized polysulfone diaphragm which had a degree of sulfonization S of 0.175 was used as the diaphragm. "Degree of sulfonization" as used herein means the ratio of sulfonic acid groups to sulfone groups: for a ratio of 1:1, the degree of sulfonization is S=1. In a diaphragm with S=0.175, the diffusion coefficient for urea is about $3 \times 10^{-11}$ cm$^2$ s$^{-1}$ and that for glucose about $4 \times 10^{-13}$ cm$^2$ s$^{-1}$. If denser diaphragms are used, i.e., diaphragms with a lower degree of sulfonization (and therefore, a more pronounced hydrophobic character), proportionality between charge and concentration is obtained even with higher urea concentrations.

In order to determine to what extent substances intrinsic to the body influence the measurements of the urea concentration, glucose and amino acids, respectively, were added to the electrolyte, in addition to the urea. It then was found that glucose (addition: 0.1%) does not influence the urea determination. An addition of amino acids with the average physiological concentration causes a measuring error of about 5%. Such a slight deviation, however, can be tolerated. It is thus demonstrated that a selective determination of urea in body liquids is possible, if the urea sensor according to the present invention is used.

What is claimed is:
1. A method for determining the urea concentration in liquids comprising:
 impressing on an electrode separated by a diaphragm permeable to urea, from the urea containing liquid, potentionstatically and cylically two potential values, the more positive potential being in the interval 0.9 V $\leq \phi$/H$_2$rev $\leq$ 2.0 V and the more negative potential being lower than 0.6 V/H rev, and evaluating the current flowing within a predetermined time interval during the more positive potential as the measuring signal
 wherein the diffusion coefficient of said diaphragm for urea is lower than $10^{-7}$ cm$^2$/s and said dia- phragm possesses both hydrophobic and hydrophilic properties such that the degree of hydrophilization of the diaphragm is within the interval $1:15 \geq H \geq 1:100$.

2. The method according to claim 1, comprising using the transferred charge as the measuring signal.

3. The method according to claim 1 or 2, comprising controlling the potential of the electrode by use of a cyclic potential jump program with two levels.

4. The method according to claim 1 wherein the more positive potential is at about 1.6 V/H$_2$rev and the more negative potential at about 0.4 V/H$_2$rev.

5. The method according to claim 1 wherein said diaphragm has a diffusion coefficient for urea of about $10^{-11}$ cm$^2$/s.

6. The method according to claim 1 wherein the thickness of said diaphragm is less than or equal to 10 micrometers.

7. The method according to claim 1 wherein the degree of hydrophilization of the diaphragm is in the interval $1:30 \geq H \geq 1:60$.

8. The method according to claim 1 wherein said diaphragm consists of weakly hydrophilized polysulfone.

9. The method according to claim 8 wherein said weakly hydrophilized polysulfone is sulfonized polysulfone.

* * * * *